United States Patent [19]

Horrobin et al.

[11] Patent Number: 5,583,159
[45] Date of Patent: Dec. 10, 1996

[54] TREATMENT OF INTERNAL RADIATION DAMAGE

[75] Inventors: David F. Horrobin; Catherine A. Scott, both of Guildford, England

[73] Assignee: Scotia Holdings PLC, England

[21] Appl. No.: 408,135

[22] Filed: Mar. 21, 1995

Related U.S. Application Data

[63] Continuation of Ser. No. 184,114, Jan. 21, 1994, abandoned.

[30] Foreign Application Priority Data

Jan. 26, 1993 [GB] United Kingdom ............... 9301446

[51] Int. Cl.⁶ .................................................. A61K 31/20
[52] U.S. Cl. .................................................. 514/560
[58] Field of Search ................................. 514/549, 560, 514/917, 922; 424/10

[56] References Cited

U.S. PATENT DOCUMENTS

| | | | |
|---|---|---|---|
| 4,996,233 | 2/1991 | Horrobin | 514/560 |
| 4,997,649 | 3/1991 | Papaconstantin et al. | 424/195.1 |
| 5,059,622 | 10/1991 | Sears | 514/549 |
| 5,271,925 | 12/1993 | Sredni et al. | 424/10 |

FOREIGN PATENT DOCUMENTS

| | | |
|---|---|---|
| 0347056B1 | 12/1989 | European Pat. Off. . |
| 0416855B1 | 3/1991 | European Pat. Off. . |
| 205689 | 6/1986 | New Zealand . |
| 224380 | 6/1991 | New Zealand . |

OTHER PUBLICATIONS

Database WPI Week 9111, Derwent AN 91–075338 Mar. 1991.
Database WPI Week 8951 Derwent AN 89–372299 Dec. 1989.
British Journal of Cancer vol. 68, No. 1, Jul. 1993 pp. 1–7 Hopewell et al "The Modulation of Radiation–induced Damage to Pig Skin by Essential Fatty Acids".
Nutrition Research vol. 5, 1985 pp. 101–105 Das et al "Benzo(a)pyrene and Gamma–Radiation–Induced . . . ".
Prostaglandins, vol. 29, No. 6, Jun. 1985 pp. 911–920 "Prostaglandins and their Precursors Can Modify Genetic Damage Induced by Gamma–Radiation and Benzo(a)pyrene".
European Patent Application 0416855 Mar. 1991, pp. 1, 3 and 5.

*Primary Examiner*—Raymond Henley, III
*Attorney, Agent, or Firm*—Nixon & Vanderhye

[57] ABSTRACT

Damage to internal tissues, and particularly to the central nervous system as a consequence of exposure to ionizing radiation is prevented or treated by administration of GLA and/or DGLA. Medicaments containing GLA and/or DGLA for such treatment or prevention may also further comprise EPA and/or DHA.

5 Claims, No Drawings

TREATMENT OF INTERNAL RADIATION DAMAGE

This is a Continuation of application Ser. No. 08/184,114, filed Jan. 21, 1994, now abandoned.

Radiotherapy is a very important form of treatment of many forms of cancer. However it is limited by the damage done to normal tissues. Ionizing radiation is harmful to many normal components of the body, notably the skin, the gastrointestinal tract and the central nervous system, but also many other tissues.

We have recently discovered (EPA 0,416,855) a new way of reducing or preventing radiation damage to the skin. This is perhaps the commonest form of radiation damage because radiation always has to pass through the skin to reach an underlying cancer and because ionizing radiation can damage the double bonds present in essential fatty acids (EFAs). Because such EFAs are particularly important in the skin, with damage to the skin always being the first indication of an EFA deficiency state, we reasoned that supplying EFAs, and especially EFAs which have undergone δ-desaturation from the main dietary EFAs linoleic acid and α-linolenic acid, might be of use. Such δ-desaturated acids include gamma-linolenic acid (GLA) and dihomo-gamma-linolenic acid (DGLA). GLA was expected to be of particular value in the skin because the skin lacks the ability to convert linoleic acid to GLA. In the above earlier application we reported that GLA and other fatty acids are indeed effective in alleviating skin damage associated with radiotherapy.

The most serious adverse effect of ionising radiation is undoubtedly damage to the central nervous system (CNS). This damage particularly limits the usefulness of ionizing radiation in the treatment of cancers of the CNS or cancers which are close to it such as cancers in the bones around the spinal cord which are very common following certain cancer types such as breast, prostate or colorectal cancers. Both patients and doctors are often reluctant to pay the price of irreversible brain or spinal cord damage even if the alternative is cancer growth.

Treatment of the central nervous system damage produced by radiation has proved an intractable problem and no successful approach has ever been developed. This is in contrast to treatment of radiation damage to the skin where a number of agents can modulate the radiation damage to some degree. It therefore seemed to us highly unlikely that a material as simple as an essential fatty acid might be beneficial. Moreover, since the central nervous system is able to convert linoleic acid to GLA, it seemed in particular unlikely that, in contrast to the skin, there would be any major value in supplying GLA as opposed to linoleic acid. However an experiment was set up in which a standard dose of radiation was delivered to the spinal cord of the pig. This dose consistently produces paraplegia within 8–12 weeks in 60–90% of the animals. 10 pigs were pretreated for one week prior to exposure to radiation and for 16 weeks after with either 6 ml/day of sunflower oil (containing linoleic acid) or 6 ml of evening primrose oil; the only important difference between sunflower oil and primrose is the GLA content of the latter. In the sunflower group three animals developed paraplegia 8 weeks after being irradiated and had to be destroyed. In the GLA group, in contrast, only one animal developed paraplegia. Two other animals showed transient neurological abnormalities at 8–9 weeks but these soon resolved and at 16 weeks the animals were alive and well.

This extent clearly shows that, completely unexpectedly, the simple compound GLA is able to provide substantial protection against radiation damage to the central nervous system, whereas linoleic acid would not. Since GLA is rapidly converted to DGLA within the body, DGLA although not formally tested is to be taken as equally effective. According to the invention further, the GLA and/or DGLA my optionally be administered in combination with n-3 EFAs which also may be used to treat tissues damaged by radiation, such as cicosapentaenoic acid (EPA) or docosahexaenoic acid (DHA).

Since damage to the CNS and damage to the skin have no apparent relation in terms of similarity of the tissues, particularly with regard to essential fatty acid metabolism, the fact that GLA can alleviate both types of radiation damage suggests that this method of treatment is to be effective in treating or preventing radiation damage to any internal, normal tissue.

The invention broadly therefore is the use of GLA and DGLA for preparing pharmaceuticals or food substances for the alleviation or prevention of radiation damage to the central nervous system and other internal tissues in radiation treatment, and for the corresponding method of actual treatment.

The GLA and other acids may be administered in any appropriate form, including free fatty adds, salts of monovalent and divalent metals, esters including mono-, di-, or tri-glycerides, cholesterol esters, phospholipids and any other convenient form delivered effectively to the desired site. The GLA may be for example given orally, enterally, parentrally (subcutaneously, intramuscularly, intravenously), rectally, vaginally, nasally, topically or by any other appropriate route.

The dose of GLA or other acids may for example range from 1 mg to 100 g per day, preferably 10 mg to 20 g, and very preferably 100 mg to 5 g/day. When prepared for topical administration or in parenteral or enteral solutions or foods the concentrations may for example range from 0.01 to 50%, preferably 0.1 to 20% and very preferably from 1 to 10%.

The following examples illustrate the invention.

EXAMPLES

1. A soft or hard gelatin capsule containing 50–500 mg of GLA in any appropriate form with the recommended dose being 2 to 10 capsules/day.

2. A tablet or pastille containing 100–200 mg of GLA in any appropriate form with the recommended daily dose being 4 to 8 per day.

3. A cream, ointment, whip, foam, pessary, suppository, or emulsion any other appropriate formulation for topical administration containing 0.1 to 10% by weight of GLA.

4. An emulsion or solution for parenteral or enteral administration containing 1% to 30% of GLA by weight.

5. A foodstuff such as granules, creams, gels, pastilles, flakes, powder or any other form known to those skilled in the art containing 0.1 to 10% of GLA by weight.

6–10 As 1–5 but with the active ingredient DGLA.

11–20 As 1–10 but in addition containing 10–300 mg of EPA or DHA per unit dose or 0.1% to 10% by weight in formulations for topical, enteral, parenteral or food use.

We claim:

1. A method of preventing damage to the central nervous system as a consequence of exposure to ionizing radiation associated with radiotherapy in patients in need thereof, comprising administering to said patient an effective amount of GLA or DGLA or both, optionally in conjunction with EPA or DHA or both.

2. The method according to claim 1, wherein the daily dose of the acid or acids is 1 mg to 100 g.

3. The method according to claim 2, wherein the daily dose of the acid or acids is 10 mg to 10 g.

4. The method according to claim 3, wherein the daily dose of the acid or acids is 100 mg to 5 g.

5. The method according to claim 1 wherein the acid or acids are administered parenterally, eternally or in a food composition.

* * * * *